(12) United States Patent
Shoda et al.

(10) Patent No.: US 6,360,121 B1
(45) Date of Patent: Mar. 19, 2002

(54) INTRACARDIAC POTENTIAL ANALYZING APPARATUS AND METHOD

(75) Inventors: Morio Shoda; Yuuji Fuda, both of Tokyo (JP)

(73) Assignee: Hiroshi Kasanaki, Tokyo (JP)

( * ) Notice: Subject to any disclaimer, the term of this patent is extended or adjusted under 35 U.S.C. 154(b) by 0 days.

(21) Appl. No.: 09/405,806

(22) Filed: Sep. 24, 1999

(30) Foreign Application Priority Data

Jul. 27, 1999 (JP) ............................................. 11-211946

(51) Int. Cl.[7] ................................................. A61B 5/04
(52) U.S. Cl. ...................................................... 600/512
(58) Field of Search .............................. 600/374, 393, 600/512, 515

(56) References Cited

U.S. PATENT DOCUMENTS

| | | | | |
|---|---|---|---|---|
| 4,922,920 A | * | 5/1990 | Thie et al. ................... | 128/699 |
| 5,595,183 A | * | 1/1997 | Swanson et al. ............. | 128/697 |
| 5,951,484 A | * | 9/1999 | Hoium et al. ................ | 600/515 |
| 6,115,630 A | * | 9/2000 | Stadler et al. ............... | 600/521 |

* cited by examiner

*Primary Examiner*—George R. Evanisko
*Assistant Examiner*—Frances P. Oropeza
(74) *Attorney, Agent, or Firm*—Jenkens & Gilchrist

(57) ABSTRACT

An intracardiac potential analyzing apparatus for calculating a progressing direction and speed of an excitation wave front from information on time from a reference point set on a time axis of an electrocardiogram to an excitation point at each of bipolar electrodes and information on the positions of three bipolar electrodes existing within a region sufficiently small to assume that the progressing direction of the excitation wave will not change and displaying them as excitation wave vectors to represent an intracardiac excitation propagation.

25 Claims, 11 Drawing Sheets

T1  T2

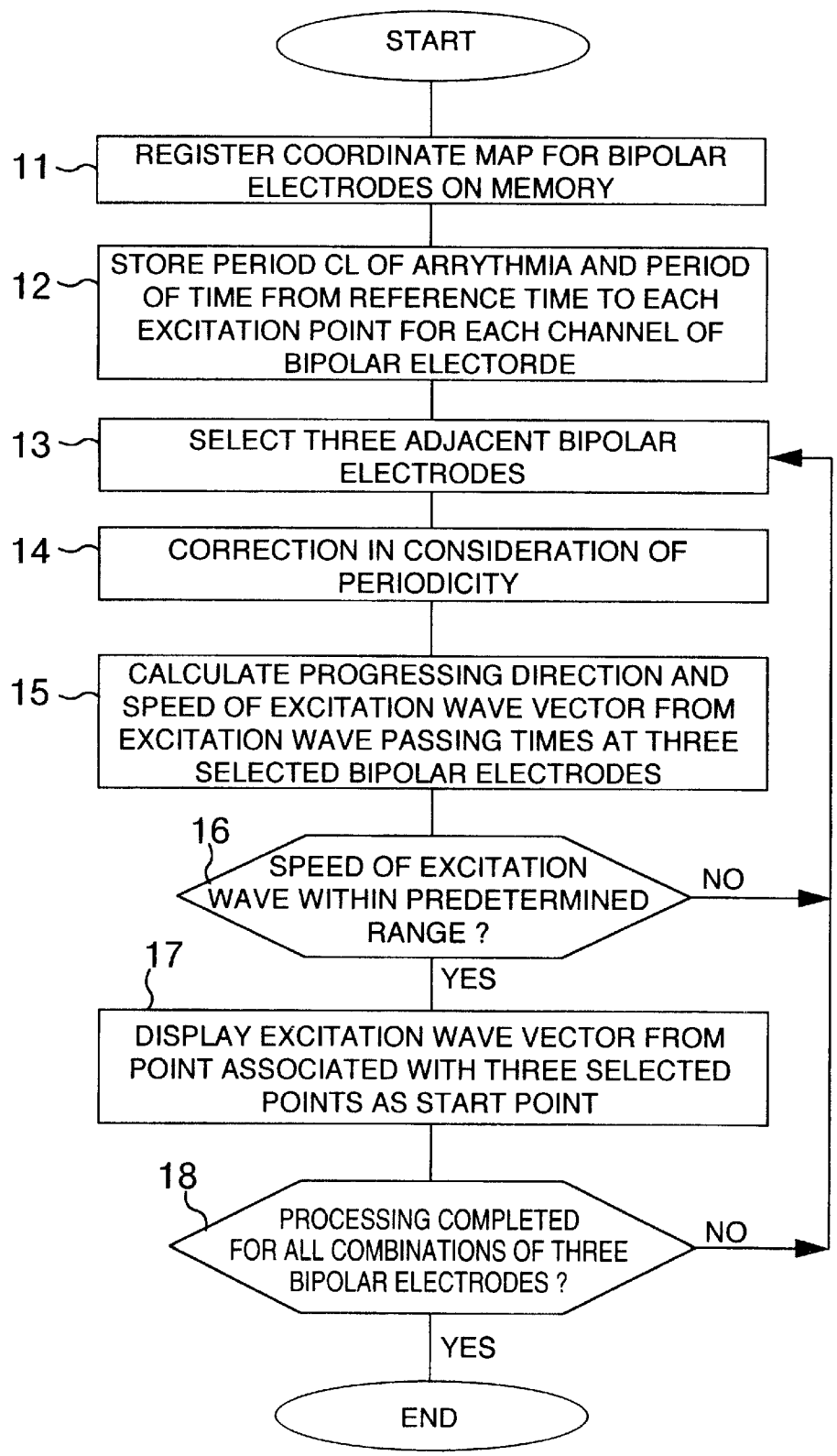

START TIME = T1

START TIME = T2

INTRACARDIAC POTENTIAL ANALYZING APPARATUS AND METHOD

BACKGROUND OF THE INVENTION

The present invention relates generally to an intracardiac potential analyzing apparatus and method in electrophysiologic cardiography using a computer, and more particularly to an apparatus and method for analyzing an excitation propagation path for an arrhythmia of reentry type (atrial tachycardia, atrial flutter, atrial fibrillation, ventricular tachycardia, ventricular fibrillation, or the like).

The arrhythmias are generally classified into three according to their mechanisms: abnormal automaticity, reentry, and triggered activity.

Arrhythmias due to abnormal automaticity and triggered activity may be understood to be arrhythmias in which an excitation wave generated at a certain site extends within the heart and reaches a boundary or collides with another excitation wave propagating through a different path to eventually extinguish without returning to the original site. An arrythmia due to reentry, in turn, may be understood to be an arrythmia that is maintained by an excitation wave passing a certain site, which propagates through the heart and returns to the same site.

At present, a method called isochronography is used for the analysis of intracardiac excitation propagation. The isochronography represents how excitation has propagated by defining a certain time as a reference start time, and connecting with lines exciting sites at a time a certain period of time after the start time. This is exactly the same as contour lines used in maps. The isochronography may be useful for analyzing an arrythmia which may be understood as an image in which the arrythmia has started at a peak, and excitation propagates toward the base, i.e., useful for arrhythmias which involve abnormal automaticity and triggered activity as their mechanisms. Stated another way, the isochronography is useful for an arrythmia that has a pattern in which excitation starts at a certain time and ends at another time.

An arrythmia due to reentry, however, is established by excitation repetitively turning about a circuit, so that it is not possible to specify the start or the end of the excitation. Specifically, in this type of arrhythmia, excitation is present anywhere without fail before a certain time, and if the excitation is traced backwardly, the path of the excitation returns to the original site. If a start time and an end time are forcibly set for conducting the isochronographic analysis, different analysis results will be produced depending on where the start time and end time are set. FIGS. 15A, 15B illustrate an example of the results produced from such an analysis. Specifically, FIGS. 15A, 15B are exemplary diagrams which have been created by setting different excitation start times T1, T2 in an electrocardiogram of FIG. 2. As is apparent from these diagrams, different results are produced when different start times are set.

Thus, the establishment of analytical technologies has long been desired for facilitating estimation of an intracardiac excitation propagation path of an arrythmia due to reentry.

SUMMARY OF THE INVENTION

The intracardiac excitation propagation may be understood just as the propagation of waves since excitation at a certain site causes excitation at an adjacent site. The intracardiac excitation propagation, however, differs from waves propagating the surface of water in that a wave cannot pass a site which has once been passed by another wave for a certain period of time. (After a myocardial tissue has excited, there is a period of time called the "refractory period" in which the myocardium cannot excite.) Therefore, phenomena such as reflection and overlapping are not found in the intracardiac excitation propagation. Specifically, a wave caused by an exciting myocardial tissue disappears when it reaches a boundary of the myocardial tissue, for example, the boundary between an atrium and a vein or the boundary between an atrium and a ventricle. In addition, when excitation waves collide with each other, they also disappear. Thus, the excitation propagation may be processed as an excitation wave which has such characteristics as mentioned above.

The present invention intends to know the nature of a progressing excitation wave by analyzing the excitation wave on the assumption that an excitation wave linearly progresses within a sufficiently small region. The progressing speed and progressing direction of a linearly progressing wave can be derived by measuring times at which the progressing wave, i.e., the excitation wave passes three different electrodes at known positions and calculating them from the measured values. Thus, the present invention calculates the progressing direction and speed of an excitation wave front for an arrythmia based on time differences (hereinafter called the "excitation wave passing time") between a reference time arbitrarily set on an electrocardiogram and times at which the excitation wave passes bipolar electrodes existing at three points within a region sufficiently small to assume that the progressing direction of the excitation wave will not change, and further based on positional information on the three bipolar electrodes, and represents an intracardiac excitation propagation by displaying it as vectors, thereby facilitating estimation of an intracardiac excitation propagation path for an arrythmia due to reentry.

The present invention can represent an intracardiac excitation propagation path with sets of vectors indicative of progressing directions and progressing speeds of local excitation waves without being affected at all by a start time and an end time of excitation. Since excitation wave vectors are calculated on the basis of time differences at respective excitation points, the representation of the intracardiac excitation propagation path will not either be affected by the position of a reference time which is set on an electrocardiogram for measuring excitation wave passing times. This results in facilitating diagnosis and treatment of a variety of arrhythmias, mainly those due to reentry. Further, by virtue of the direct representation of the progressing directions and progressing speeds of excitation waves as vectors, the present invention facilitates estimation of the mechanism involved in an arrhythmias.

BRIEF DESCRIPTION OF THE DRAWINGS

FIG. 9 is a flow chart illustrating an embodiment of the analysis processing for analyzing a periodic arrythmia;

DETAILED DESCRIPTION OF THE EMBODIMENTS

An intracardiac potential analysis according to the present invention is directed to analyze data resulting from measurements of myocardial excitation. While myocardial excitation may be recorded by a variety of methods, typically, fine catheter electrodes accommodating a plurality of electrodes are inserted into a heart through blood vessels, and the plurality of electrodes are extended within the heart to measure and record excitation states of the myocardium at multiple points. In this event, myocardial excitation times and positions of measuring electrodes are recorded in correspondence.

Figure 1A:
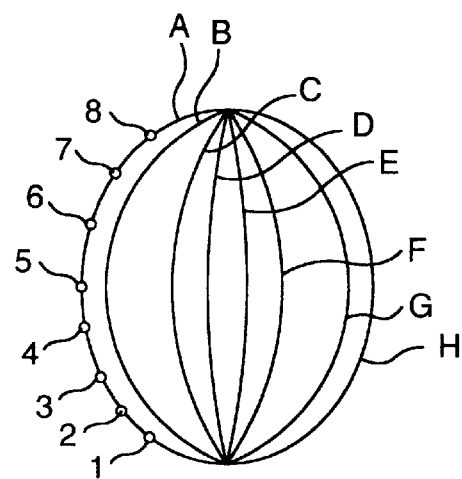
FIG. 1A shows electrodes for use in measurements of myocardial excitation.
Figure 1B:
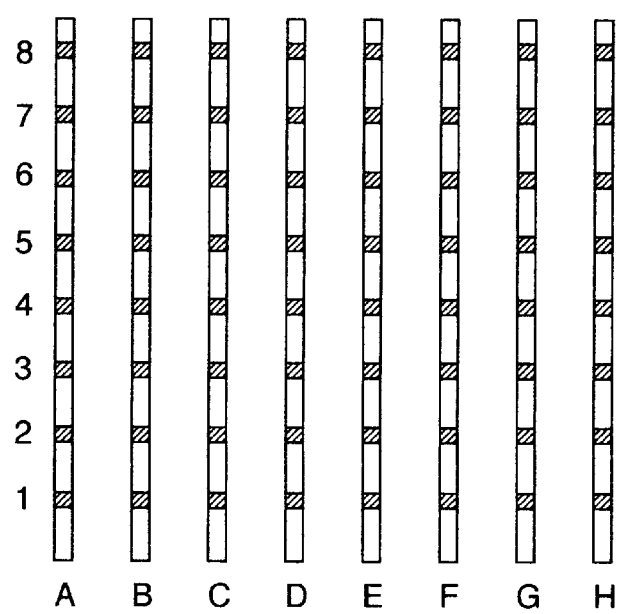
FIG. 1B represents the arrangement of the electrodes in FIG. 1A on a top plan view.

FIGS. 1A, 1B show an example of a 64-pole basket catheter for use in the intracardiac potential analysis of the present invention. The illustrated basket catheter has eight electrodes mounted on each of eight arcuate electric wires A through H, so that a total of 64 electrodes are positioned in the form of globe, with their relative positions remaining fixed. FIG. 1A shows how the electrodes are extended in the form of globe in the heart. The respective electrodes are labelled A1, A2, . . . , H7, H8 as a combination of a letter designating a wire (A–H) and a number designating an electrode (1, 2, 3, . . . , 8), as shown in FIG. 1B.

Here, a bipolar electrode formed of electrodes A1, A2 is labelled A12, and a total of 32 sets of like bipolar electrodes are similarly labelled A12, A34, A56, . . . , H56, H78. Then, potential differences between the bipolar electrodes of the respective sets are recorded in correspondence to the positions of the respective bipolar electrodes. The position of each bipolar electrode may be defined at the position of either of the two electrodes, an intermediate point between the two electrodes, or any position near the two electrodes which may be set in association with the positions of the two electrodes.

Figure 2:
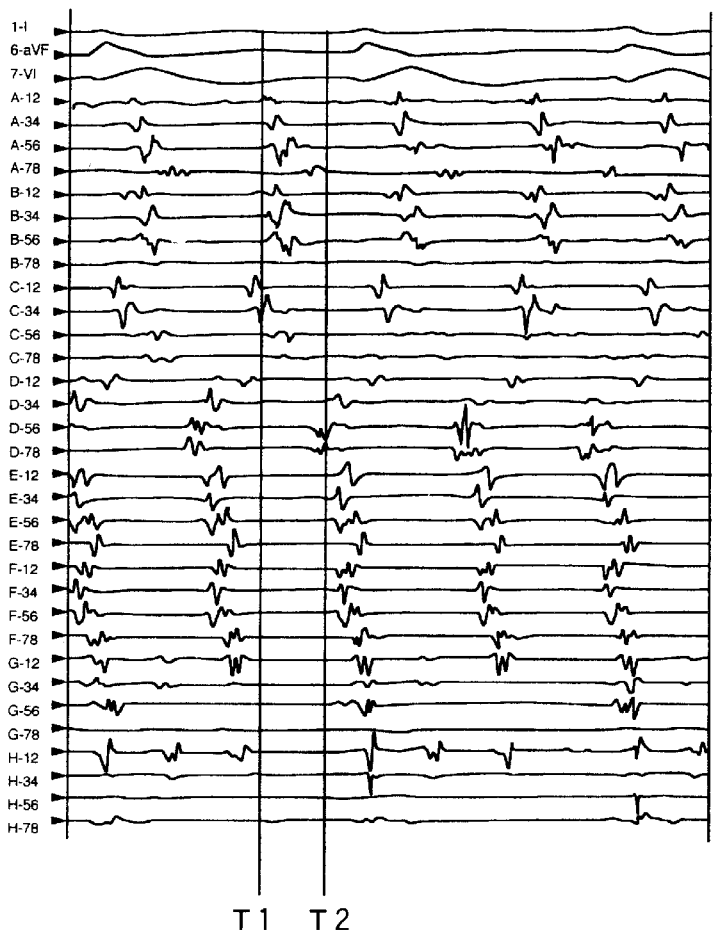
FIG. 2 is a diagram illustrating the result of a measurement made with bipolar electrodes.

FIG. 2 shows an output of a polygraph which shows an example of an arrythmia due to reentry which has been recorded using 32 sets of bipolar electrodes. Each of channels (A12, A34, . . . , H78) in FIG. 2 shows an intracardiac electrocardiogram. In the present invention, myocardial excitation resulting from one or a plurality of beats is measured at a plurality of measuring points for analysis.

Figure 3:
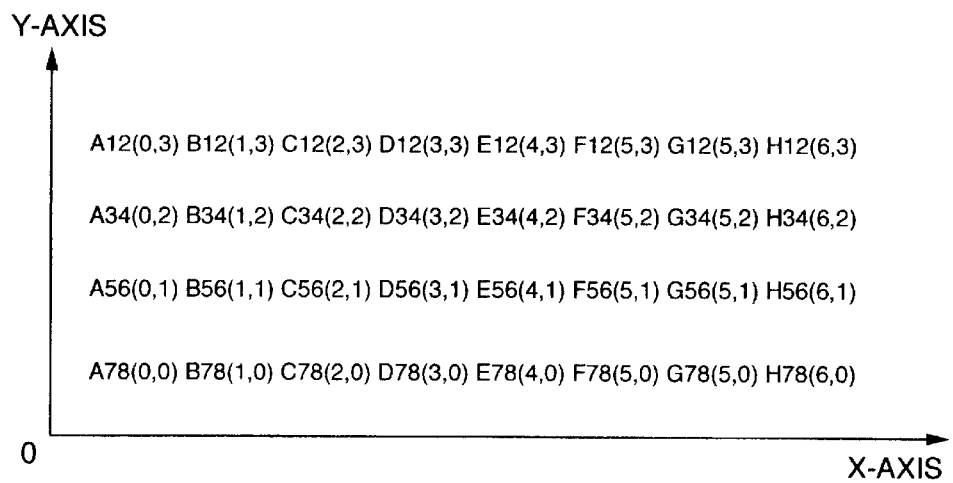
FIG. 3 represents the bipolar electrodes on a top plan view.

In this embodiment, since the result of analysis is represented as vectors on a two-dimensional plane, the respective positions of the plurality of bipolar electrodes distributed in a three-dimensional space are translated into corresponding positions in a two-dimensional plane. FIG. 3 shows an example of a coordinate map which represents the relationship of relative positions of the bipolar electrodes translated on a two-dimensional plane. The respective measuring positions are uniquely determined when a certain position is defined as a reference. In the shown example, an emphasis is placed on the relative positional relationship among the respective bipolar electrodes. In addition, assuming that each of the bipolar electrodes is placed on a plane defined by an X-axis and a Y-axis, A12 is positioned at the X-coordinate equal to zero and the Y-coordinate equal to three (0, 3), and the coordinates of the remaining bipolar electrodes are determined as shown in FIG. 3. A final result of analysis is also drawn on this positional relationship. The coordinate map for the bipolar electrodes of FIG. 3 has been previously registered on a memory by a program.

Figure 4:
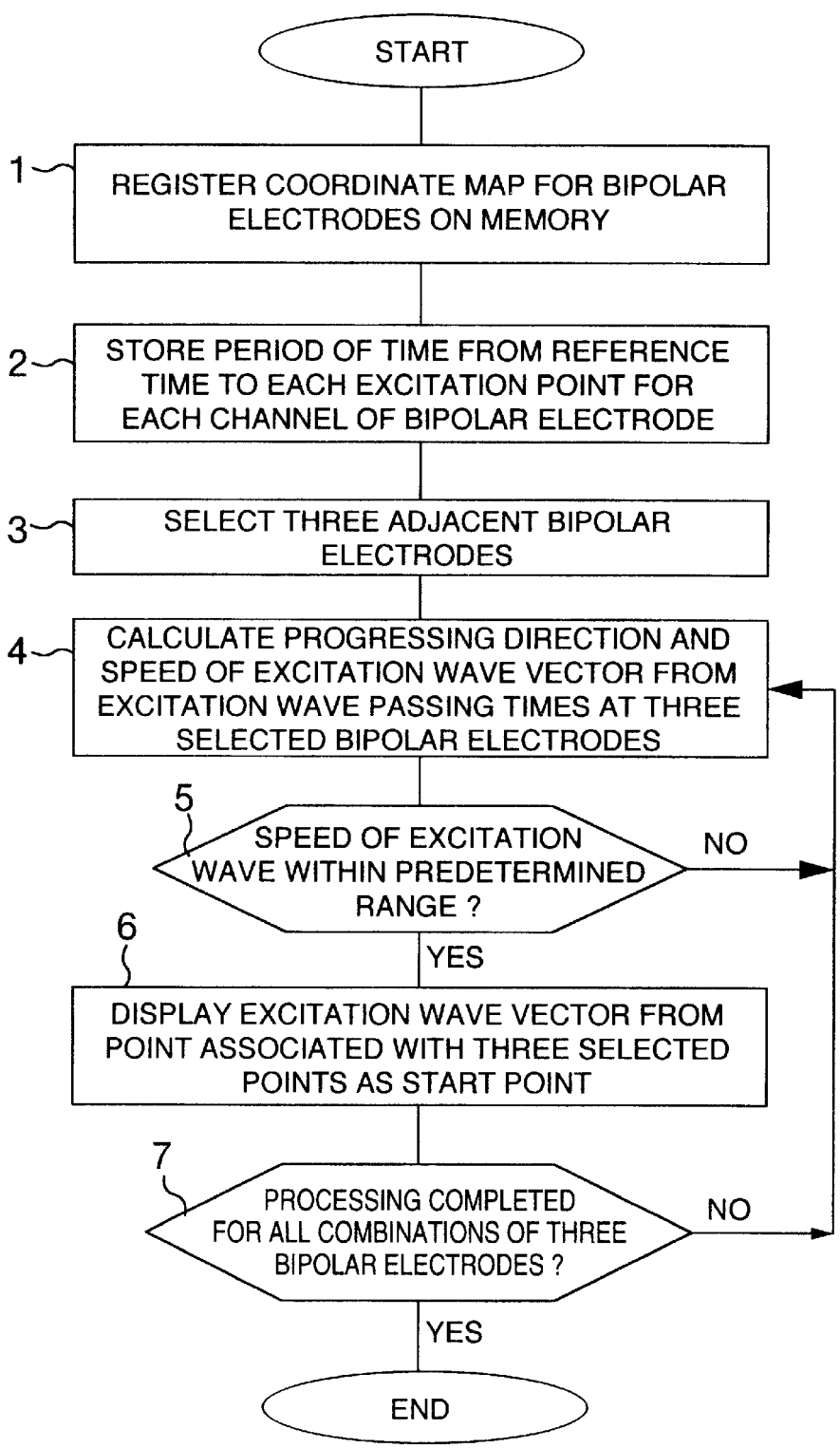
FIG. 4 is a flow chart illustrating an embodiment of the analysis processing according to the present invention.

FIG. 4 illustrates a flow chart for the analysis processing executed by the analyzing apparatus of the present invention.

Step 1: The coordinate map for a plurality of bipolar electrodes, as shown in FIG. 3 as an example, is registered in a memory.

Step 2: On a time axis of the electrocardiogram in FIG. 2, a period of time from an arbitrarily set reference time T1 (or T2) to a time at which excitation initiates is measured as an excitation wave passing time which is inputted to the analyzing apparatus of the present invention.

The reference time may be set anywhere on the time axis of the electrocardiogram. The present invention can produce the same result irrespective of where to set the reference time.

The inputted excitation wave passing times are stored in the memory corresponding to associated bipolar electrodes. The measurement of the excitation wave passing time may be made by a user on the electrocardiogram or may be automatically read and inputted by a machine.

Step 3: Three adjacent bipolar electrodes are selected from among all the bipolar electrodes. In this embodiment, since the positions of the bipolar electrodes have been originally established, 96 combinations have been previously determined for sets of three bipolar electrodes as (A12, A34, B12), (A12, A34, B34), and so on.

Step 4: With respect to the three selected bipolar electrodes, an excitation wave vector passing three points, at which the selected bipolar electrodes exist, is calculated from the excitation wave passing times inputted at step 2 by the following equation. The calculated vector is stored in the memory.

The positions of the three bipolar electrodes are set at A(Ax, Ay, Az), B(Bx, By, Bz), C(Cx, Cy, Cz), respectively, in an orthogonal three-dimensional coordinate system defined by mutually orthogonal x-, y-, z-axes. Assuming that excitation wave passing times corresponding to the three points A, B, C are represented by At, Bt, Ct, respectively, the excitation wave vector:

$$\vec{v} = v(v_x, v_y, v_z)$$

is calculated by the following equation:

$$\vec{v} = \frac{t_1|\vec{y}|^2 - t_2\vec{x}\cdot\vec{y}}{t_2^2|\vec{x}|^2 + t_1^2|\vec{y}|^2 - t_1 t_2 \vec{x}\cdot\vec{y}} \vec{x} + \frac{t_2|\vec{x}|^2 - t_1\vec{x}\cdot\vec{y}}{t_2^2|\vec{x}|^2 + t_1^2|\vec{y}|^2 - t_1 t_2 \vec{x}\cdot\vec{y}} \vec{y} \quad (1)$$

where $\vec{x} = \vec{AB}$, $\vec{y} = \vec{AC}$, $t_1 = Bt - At$, and $t_2 = Ct - At$.

Equation (1) can be applied as it is to a calculation of a like vector in a two-dimensional plane. From this equation, an excitation wave vector passing the three points is calculated, and then the progressing direction and speed are determined for the excitation wave, i.e., the vector.

Step 5: A determination is made as to whether it can be assumed that the speed of the excitation wave front has not changed at the three selected points. Predetermined progressing speeds may be set as upper limit and lower limit thresholds for the criteria for the determination. The flow proceeds to step 6 when determining that it can be assumed that the speed has not changed. When it is determined that the speed has changed or if a potential cannot be recorded at some point, the flow returns to step 3 to select a next combination of bipolar electrodes.

Step 6: A predetermined point, which has been set associated with the three selected bipolar electrodes, is defined as a start point of the vector, and the vector is displayed on a display device in the calculated progressing direction, in association with the coordinate map registered at step 1. In this event, while the magnitude of the vector is a relative value of the progressing speed, a unit length is arbitrarily set such that the vector is appropriately displayed. Even if a vector is determined to be out of a predetermined range at step 5, this vector may also be displayed together with an indication that the vector is out of range.

Selected as the start point of the vector may be, for example, the center of the three selected points, or the one having the smallest excitation wave passing time of the three points. When the center of the three points is selected as the start point, the center point $P(P_x, P_y, P_z)$ is calculated by the following equations.

$$P_x = \frac{A_x + B_x + C_x}{3}$$

$$P_y = \frac{A_y + B_y + C_y}{3}$$

$$P_z = \frac{A_z + B_z + C_z}{3}$$

Figure 5:
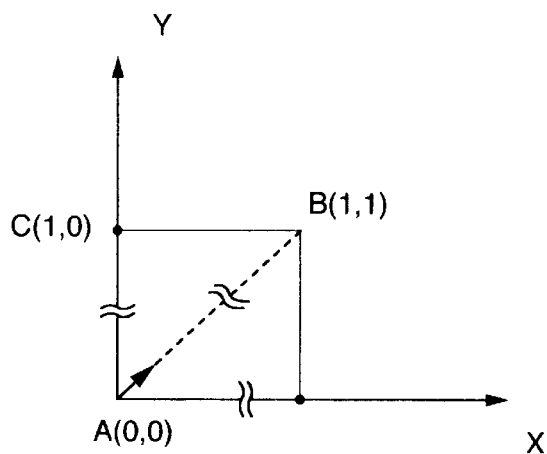
FIG. 5 shows how an excitation wave vector is drawn.

FIG. 5 shows an example of how an excitation wave vector is drawn as an arrow. Specifically, FIG. 5 shows an example in which A78 (0, 0), B56 (1, 1), A56 (0, 1) in FIG. 3 are selected as three points A, B, C, and the start point of the vector is defined at the point A, with At=10 ms, Bt=30 ms and Ct=20 ms.

From $A(0, 0)$, $B(1, 1)$, $C(0, 1)$, $\vec{x} = \vec{AB} = (1, 1)$ and $\vec{y} = \vec{AC} = (0, 1)$ are found. Also, t1=Bt−At=30−10=20 ms, and t2=Ct−At=20−10=10 ms. Substituting these values into Equation (1):

$$v_x = \frac{20 \times (0^2 + 1^2) - 10 \times (1 \times 0 + 1 \times 1) \times 1}{10^2 \times (1^2 + 1^2) + 20^2 \times (0^2 + 1^2) - 20 \times 10 \times (1 \times 0 + 1 \times 1)}$$

$$= 0.025$$

=0.025

Similarly, $v_y = 0.025$.

Thus, the vector $\vec{v}$ is expressed as follows, and illustrated as in FIG. 5:

$$\vec{v} = (0.025, 0.025)$$

Step 7: It is examined whether or not the processing at steps 3–6 has been executed for all combinations of three bipolar electrodes. The flow returns to step 3 if NO, and the analysis processing is terminated if YES.

Figure 6:
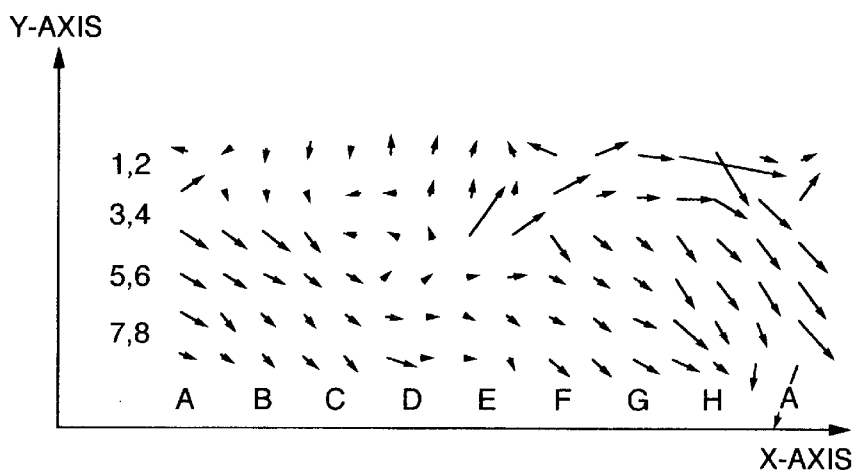
FIG. 6 shows the result of an analysis on measured data in FIG. 2.

FIG. 6 shows an example of the final result displayed by the analyzing apparatus of the present invention. Excitation wave vectors are displayed on the coordinate map of FIG. 3 which indicates the relative positional relationship among the bipolar electrodes. A shorter stroke of an arrow indicates a lower excitation propagation speed. From the directions of arrows, the progressing directions of excitation waves are also apparent. In this embodiment, it can be seen that the waves are extending near E34.

Figure 7:
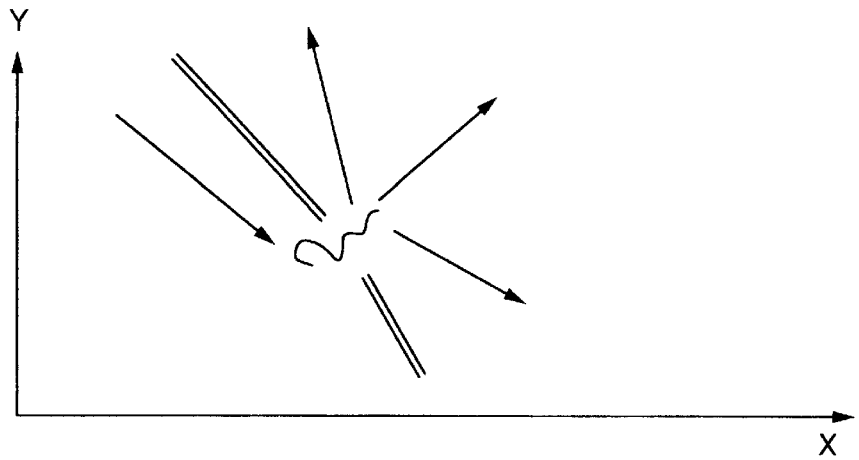
FIG. 7 shows an example of estimated excitation propagation paths.

FIG. 7 represents a path of excitation propagation assumed from FIG. 6 as a schematic diagram. It can be seen in FIG. 7 that the right atrium includes portions (indicated by double lines) which cannot be traversed by an excitation wave. The portions appear to be scars possibly resulting from an incision during an operation. A mechanism assumed from FIG. 7 is such that an excitation wave passes through a narrow region (indicated by a wave line) between the portions, through which the excitation wave can pass at a low speed, and circulates around a scar tissue. Once the path of the excitation wave has become apparent to such a degree, it is understood that this arrythmia can be cured by a treatment that provides the narrow region between the scars of the incision, which is the narrowest portion of the path, with rapid frequency energy through an electrode catheter to alter the myocardial tissue such that no excitation wave can pass through the narrow region (this treatment is called the "catheter ablation").

FIGS. 8A, 8B, 8C and 9 are diagrams for explaining the principles of an analysis on an arrythmia having a constant period. Excitation points measured by electrodes A12, A34, B12 are designated by E1, E2, E3; the period of an excitation wave by CL (in milliseconds); and excitation points after one period by the same reference numerals with a prime (').

In a polygraph which has recorded for at least one period of an arrythmia having a constant period, if a reference time is set at an arbitrary position, excitation does not always propagate sequentially from the smallest one to the largest one of measured excitation wave passing times. It is therefore necessary to correct excitation wave passing times on the related three excitation points.

Figure 8A:
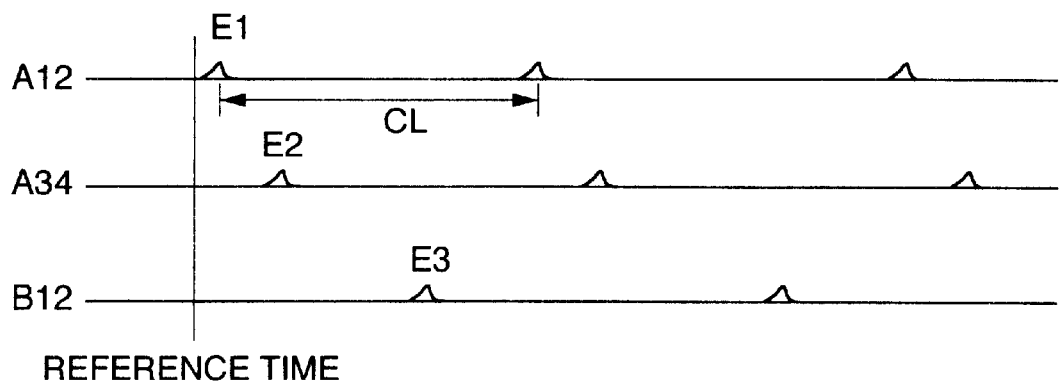
FIGS. 8A, 8B and 8C are diagrams for explaining the principles of a correction for an excitation wave passing time when a periodic arrythmia is analyzed.

In the case of FIG. 8A, if a time difference between the points E1 and E2 and a time difference between the points E2 and E3 are both less than CL/2, it is determined that the excitation is propagating sequentially in the order of E1, E2, E3, i.e., from the point nearest to the reference time. Thus, times from the reference time are substituted, as they are, into Equation (1) as excitation wave passing times at the points E1, E2, E3.

Figure 8B:
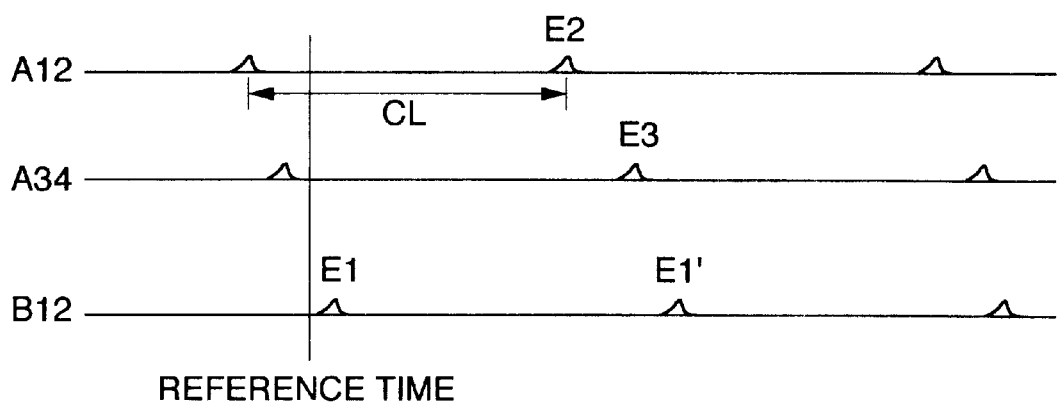

In the case of FIG. 8B, while excitation can be seen at E1, E2, E3 in order of increasing interval from the reference time, actual excitation can be thought to occur in the order of E2, E3, E1'. In this event, it is examined whether or not a time difference between the points E1 and E2 is equal to or more than CL/2. When the time difference is equal to or more than CL/2, the point E1' one period after E1 is employed instead of E1, and excitation wave passing times at the three points E2, E3, E1' are substituted into Equation (1).

Figure 8C:
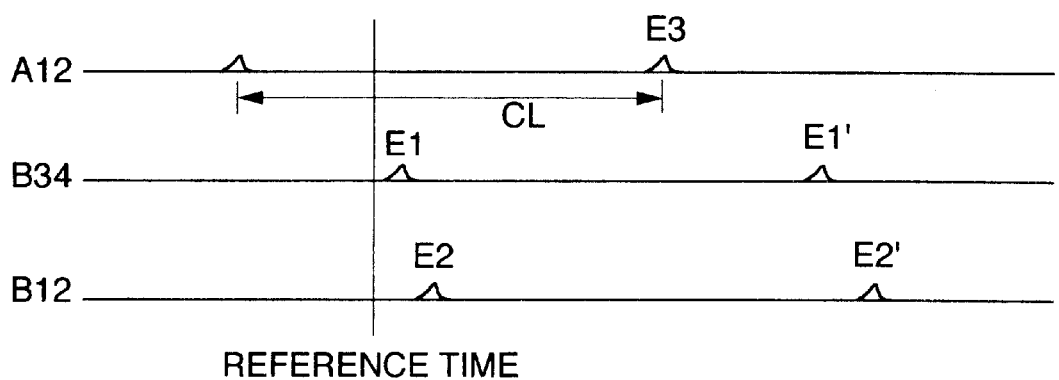

In the case of FIG. 8C, while excitation can be seen at E1, E2, E3 in order of increasing interval from the reference time, actual excitation can be thought to occur in the order of E3, E1', E2'. In this event, it is examined whether or not a time difference between the points E1 and E2 and a time difference between the points E2 and E3 are equal to or more than CL/2. If only the time difference between the points E1 and E2 is equal to or more than CL/2, the points E1', E2', which are one period after E1, E2, are employed instead of E1, E2, respectively, and excitation wave passing times at the three points E3, E1', E2' are substituted into Equation (1).

FIG. 9 is a flow chart illustrating an embodiment for performing the foregoing correction. This flow chart is basically the same as the flow chart of FIG. 4 except for a correction in consideration of the periodicity.

Step 11: A coordinate map for a plurality of bipolar electrodes is registered in a memory.

Step 12: The period CL of an arrythmia, and an excitation wave passing time up to an excitation point is inputted for each channel of bipolar electrode. Excitation wave passing times are stored corresponding to the bipolar electrodes.

Step 13: Three adjacent bipolar electrodes are selected from among all bipolar electrodes.

Step 14: A correction in consideration of the periodicity is made according to the flow of FIG. 10.

Figure 10:
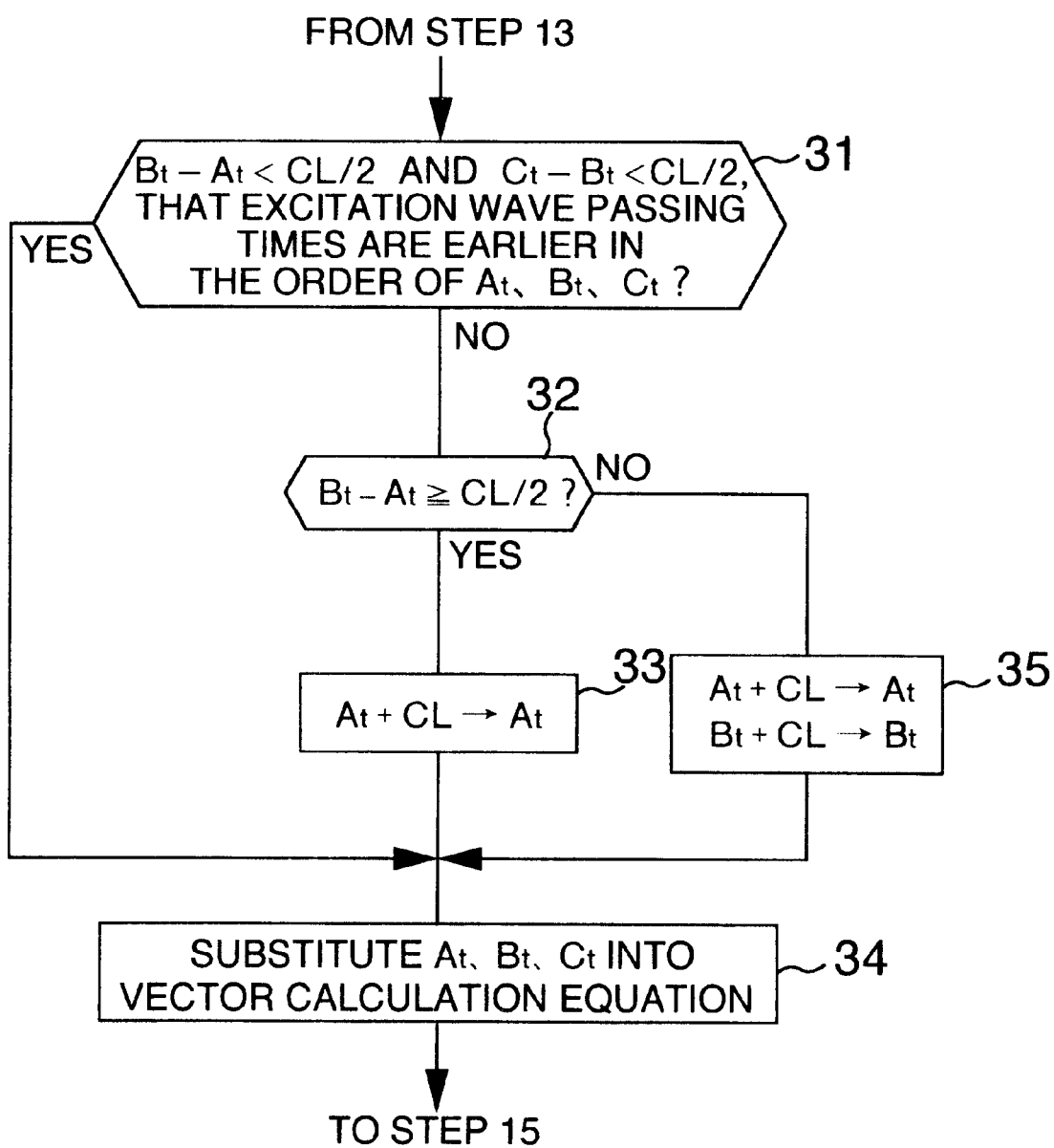
FIG. 10 is a flow chart illustrating an embodiment of a correction procedure.

Explaining now the processing flow of FIG. 10, it is first examined whether $Bt-At<CL/2$ and $Ct-At<CL/2$ are satisfied on the assumption that the excitation wave passing times are earlier in the order of At, Bt, Ct (step 31). If YES, At, Bt, Ct are substituted into Equation (1) without correction. If NO, it is examined whether $Bt-At \geq CL/2$ is satisfied (step 32). If YES, CL is added to At to derive a new At (step 33), and the corrected At, and Bt, Ct are substituted into Equation (1) (step 34). If NO, $Bt-At<CL/2$ and $Ct-Bt \geq CL/2$ are satisfied, so that CL is added to each of At, Bt to derive new At, Bt (step 35). Then, the corrected At and Bt, and Ct are substituted into Equation (1) (step 34).

After the correction, the flow proceeds to step 15.

Since steps 15–18 correspond to steps 4–7 in FIG. 4, explanation thereon is omitted.

Figure 11:
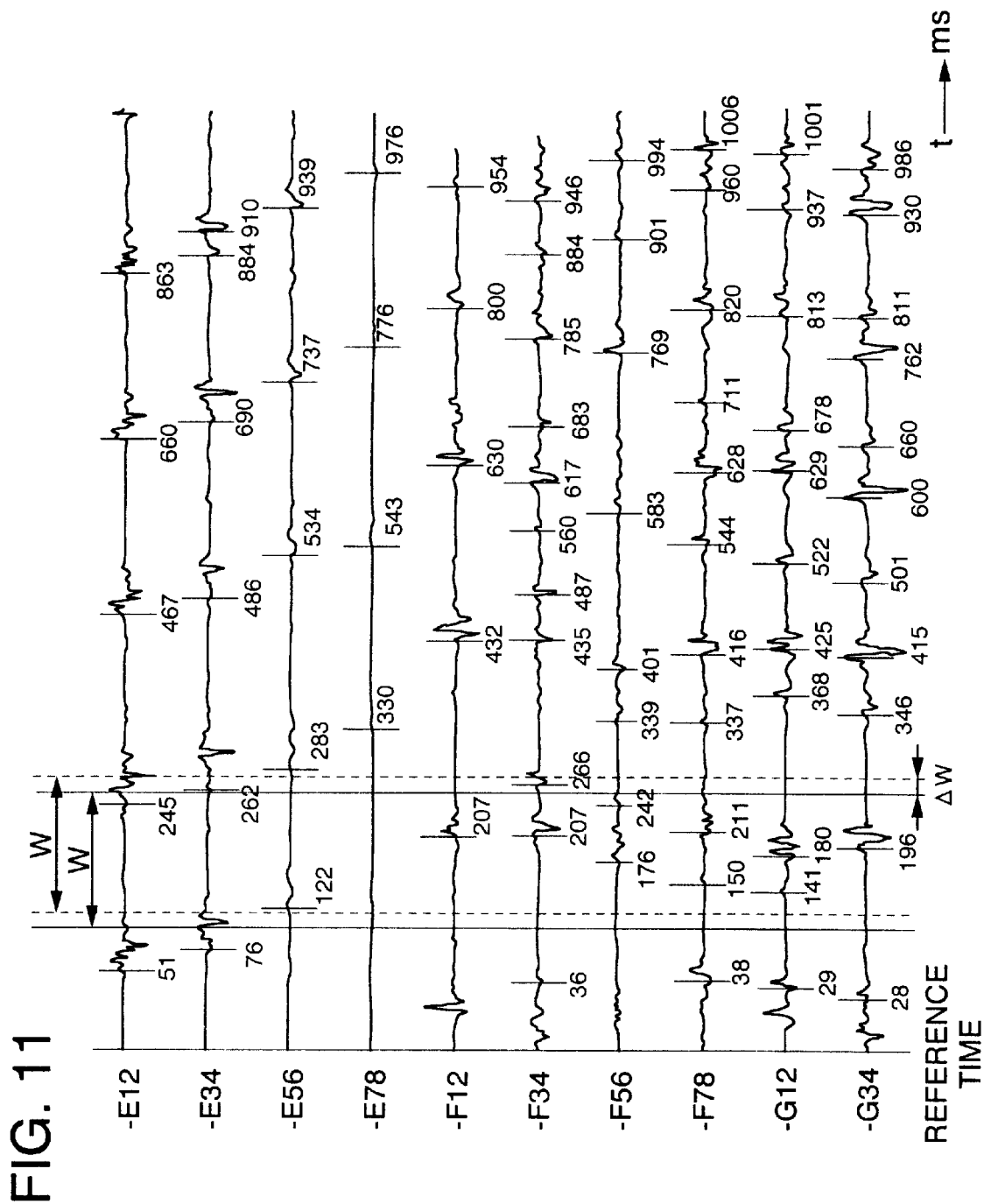
FIG. 11 shows an embodiment of an analysis on a non-periodic arrythmia.

FIG. 11 shows an embodiment for analyzing an arrythmia which does not have a constant period. In FIG. 11, a numerical value shown with each excitation point indicates a period of time in milliseconds from a reference time.

In the case of non-periodic arrhythmias such as atrial fibrillation, ventricular fibrillation or the like, if the same site excites twice, excitation waves passing the site propagate in different directions. Thus, for representing a situation of excitation waves within a certain time range with vectors, it is necessary to measure all times at which excitation occurs within the time range. Nevertheless, if excitation wave vectors were simultaneously represented at all times, the vectors would overlap with each other, resulting in failing to clarify the situation. However, if a sufficiently short period of time, for example, a time width of 100 ms is set for observing excitation, the same site will never excite twice within such a short period of time. Thus, an analysis window having a time width of 100 ms is set to calculate excitation wave vectors for excitation points within the window and display the excitation wave vectors thus calculated. Next, the window is shifted, for example, by ΔW equal to 10 ms to calculate excitation wave vectors for excitation points within the shifted window and display the excitation wave vectors thus calculated. In this way, when the analysis window is shifted each time by ΔW to display vectors within the window in an animation manner, changes in excitation waves can be represented over time. The time width of the analysis window may be set in a range of 10 to 400 ms. Preferably, the time width may be set in a range of 50 to 200 ms.

Figure 12:
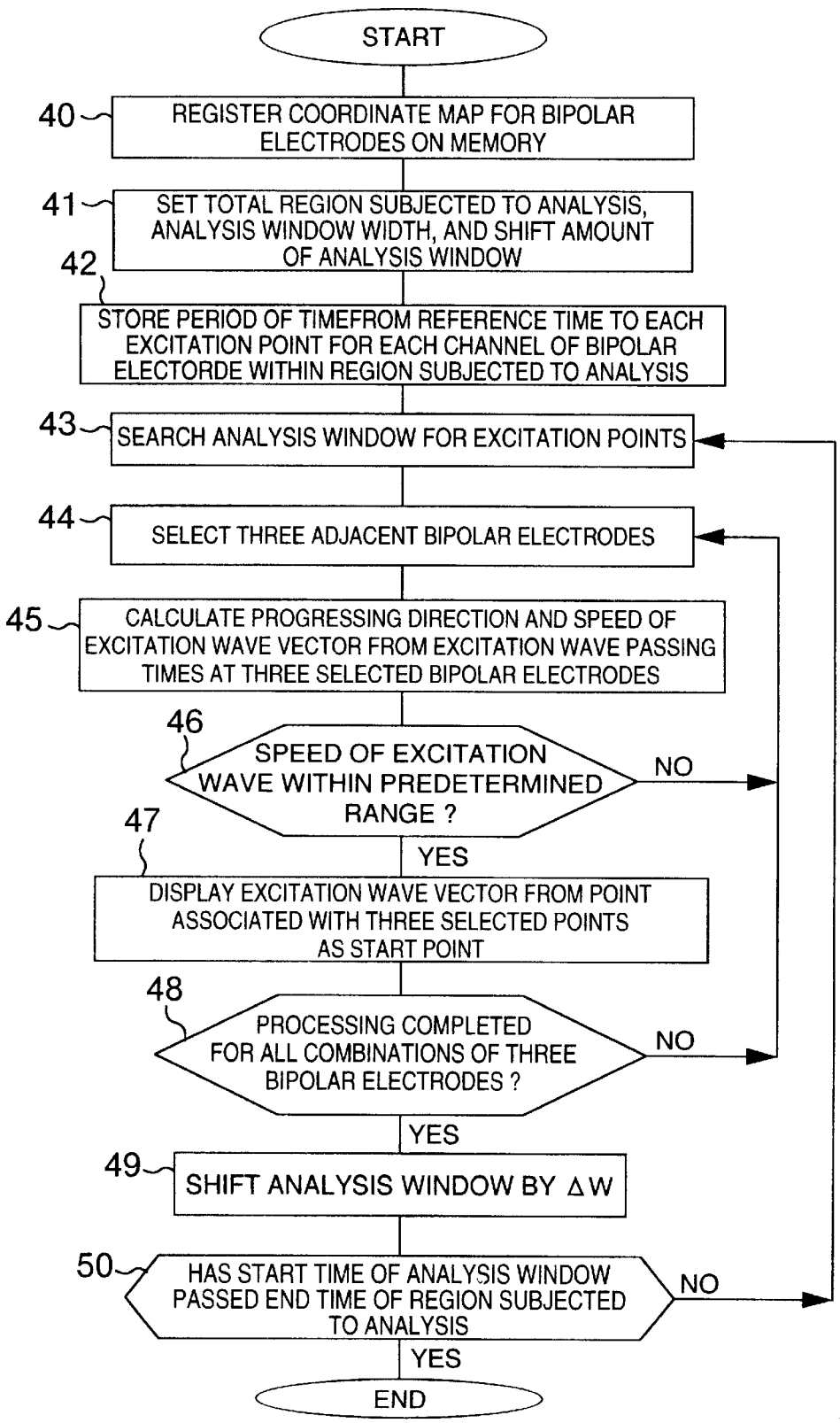
FIG. 12 is a flow chart illustrating an embodiment of the analysis processing for analyzing a non-periodic arrythmia.

FIG. 12 is a flow chart illustrating an embodiment of the analysis processing for analyzing a non-periodic arrhythmia. This flow chart is basically the same as the flow chart of FIG. 4 except for steps involved in the processing related to the analysis window.

Step 40: A coordinate map for a plurality of bipolar electrodes is registered in a memory.

Step 41: A total region subjected to the analysis, the width W of an analysis window, and a shift amount ΔW of the analysis window are inputted for setting.

Step 42: Within a period of time set for analysis, a time from a reference time to each excitation point is inputted for each channel of bipolar electrode, and stored in the memory.

Step 43: The analysis window W is searched for excitation points. If a plurality of excitation events are recognized at a single site, one of the excitation events is selected. For example, the one nearest to the start point or the end point of the analysis window may be selected.

Since steps 44–48 correspond to steps 3–7 in FIG. 4, explanation thereon is omitted.

Step 49: Once all processing has been completed within the same analysis window, the analysis window is shifted by ΔW.

Step 50: It is examined whether or not the start time of the analysis window has passed the end time of the total region subjected to the analysis. If NO, the flow returns to step 43 to execute the analysis processing in a new analysis window. If YES, the analysis processing is terminated.

Figure 13:
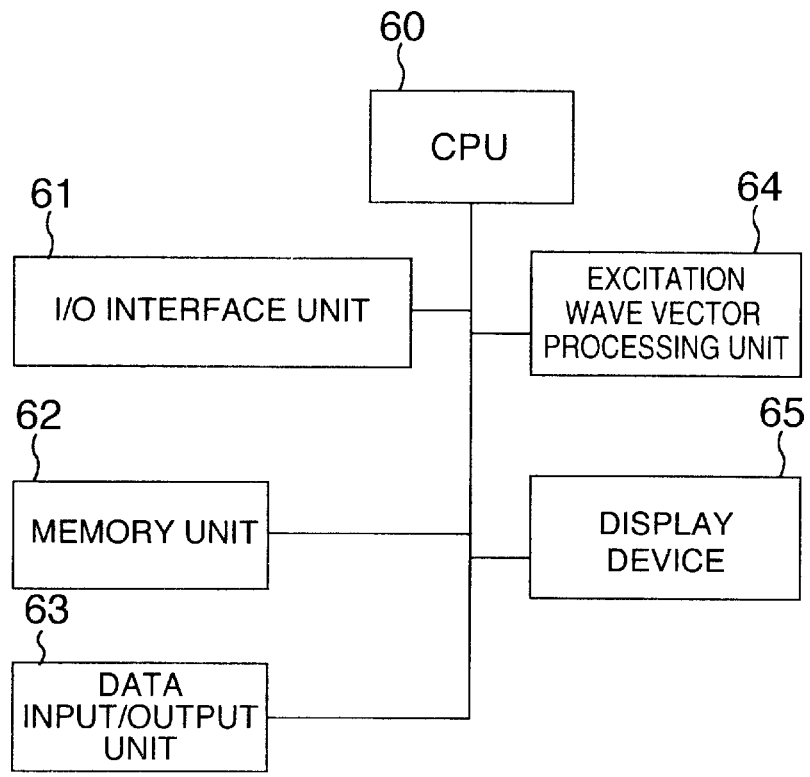
FIG. 13 is a block diagram illustrating an embodiment of an intracardiac potential analyzing apparatus according to the present invention.

FIG. 13 illustrates in block diagram form one embodiment of an intracardiac potential analyzing apparatus according to the present invention. The illustrated intracardiac potential analyzing apparatus comprises a CPU 60 for controlling the operation of the entire apparatus. An input/output interface unit 61 receives data resulting from myocardial measurements from an external myocardial measuring apparatus, outputs the result of analysis to an external device such as a printer or the like, and enables a connection with a data input device such as a keyboard, a mouse or the like. A memory unit 62 includes RAM and ROM for storing programs for executing the respective steps of the analysis flows according to the present invention, as previously illustrated in FIGS. 4, 9, 12, as well as a coordinate map for electrodes, input data such as excitation wave passing times and so on, data derived in the middle of analysis, the result of analysis, and so on. A data input/output unit 63 inputs and outputs data to and from a data recording medium such as a magnetic disk, an optical disk, a magneto-optical disk, a semiconductor memory or the like. An excitation wave vector processing unit 64 executes the analysis flows from excitation wave passing times related to sets of three electrodes, and the positional information of the electrodes on the coordinate map. A display device 65 displays the result of analysis in the form of vectors.

It should be noted that the programs for executing the respective steps of the analysis flows according to the present invention, as previously illustrated in FIGS. 4, 9, 12, may be provided as a computer readable recording medium which has the programs recorded thereon, for example, a magnetic disk, an optical disk, a magneto-optical disk, a semiconductor memory, or the like. In this case, the analysis programs according to the present invention may be implemented in a computer which includes an input/output interface that has a unit for reading a computer readable recording medium, a CPU, a memory, a display device, and so on.

While the foregoing embodiment has been described for an example in which the result of analysis is displayed on a two-dimensional plane, the coordinate map for bipolar electrodes, corresponding to that of FIG. 3, may be set in a three-dimensional space to three-dimensionally display the result of analysis. Also, while in the foregoing embodiment, the electrodes have been described as bipolar electrodes, the present invention can also be adapted as it is to monopolar electrodes.

Figure 14:
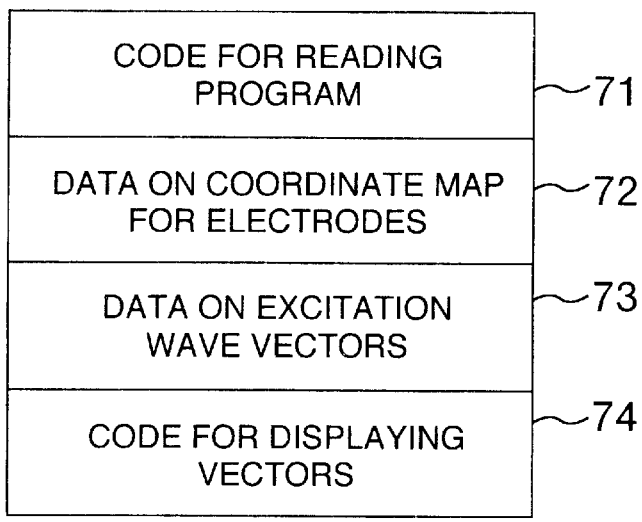
FIG. 14 is a diagram for explaining the structure of data on a recording medium which contains a program for displaying excitation wave vectors as the result of an analysis.
Figure 15A:
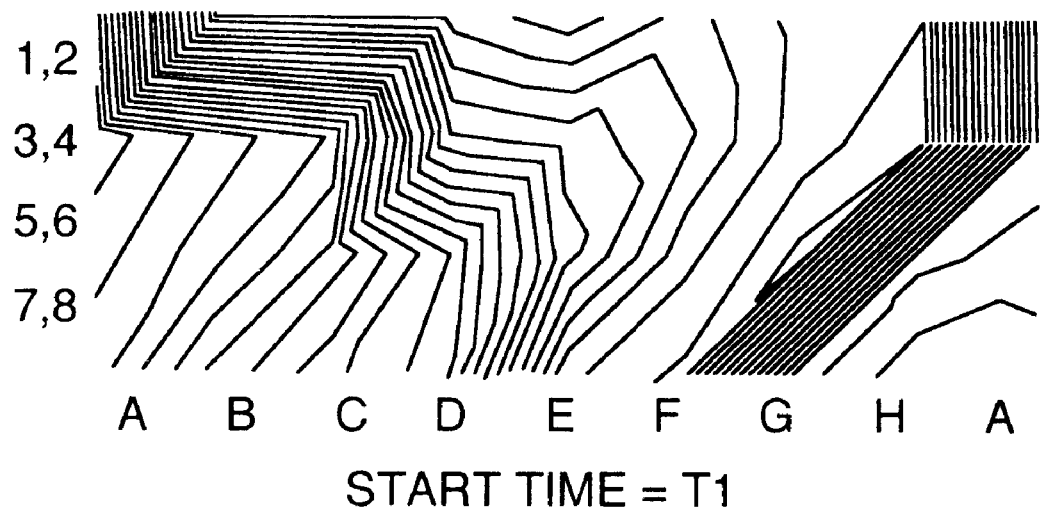
FIGS. 15A, 15B show the results of an analysis on an arrythmia due to reentry represented by isochronographs which have been drawn with different start times indicated in FIG. 2.
Figure 15B:
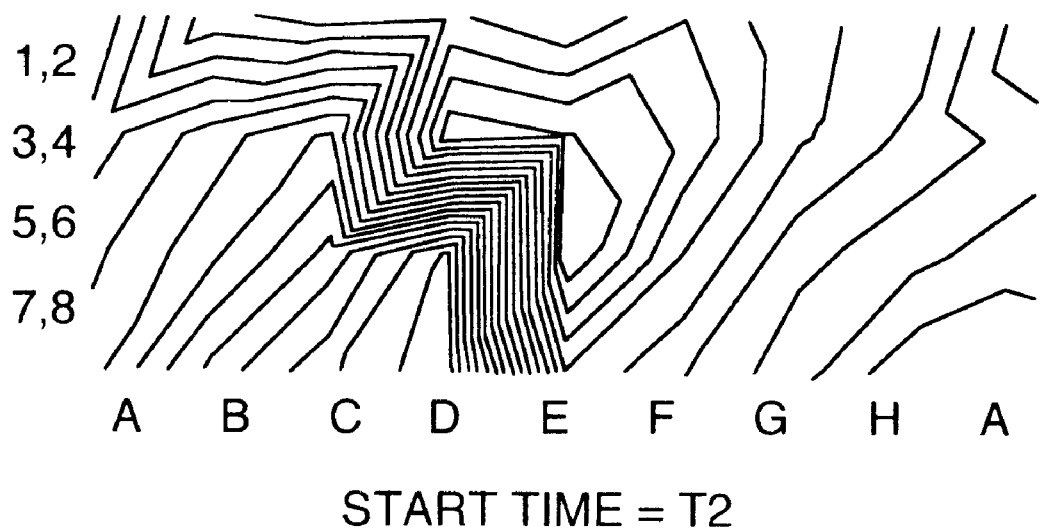

FIG. 14 shows the data structure for the result of analysis stored on a recording medium. When this recording medium is loaded in another computer for retrieval of data recorded thereon, the result of analysis may be viewed at any other place. The recording medium may be a magnetic disk, an optical disk, a magneto-optical disk, a semiconductor memory, or the like.

The data structure includes a code region 71 for storing a code for reading a program for displaying the result of analysis; a region 72 for storing data associated with the coordinate map for electrodes; a region 73 for storing data on excitation wave vectors derived by calculations; and a code region 74 for storing a code for displaying vectors associated with the coordinate map for electrodes.

It should be understood that the present invention is not limited to the disclosed embodiments, and that the present invention encompasses a variety of such modifications that fall under the spirit and scope of the claims.

We claim:

1. An intracardiac potential analyzing apparatus utilizing a computer comprising:

first means for storing a relative positional relationship among a plurality of electrodes as a coordinate map;

means for selecting a plurality of sets of three adjacent electrodes from among said plurality of electrodes;

means for calculating a vector of an excitation wave which has passed said three adjacent electrodes for each of said plurality of sets of three adjacent electrodes; and means for displaying said plurality of calculated vectors in association with said coordinate map.

2. An intracardiac potential analyzing apparatus according to claim 1, wherein said means for calculating a vector includes:

second means for storing an excitation wave passing time from a reference time, serving as a reference, to a time at which an excitation wave passes each of said electrodes, said reference time being arbitrarily set on a time axis of an electrocardiogram; and means for calculating an excitation wave vector with respect to said three adjacent electrodes from positional information read from said first means and said excitation wave passing times read from said second means.

3. An intracardiac potential analyzing apparatus according to claim 2, wherein said means for calculating a vector includes means for setting positions of three electrodes in an orthogonal three-dimensional coordinate system defined by three mutually orthogonal x-, y-, and z-axes as A(Ax, Ay, Az), B(Bx, By, Bz), and C(Cx, Cy, Cz), and calculating an excitation wave vector:

$$\vec{v} = v(v_x, v_y, v_z)$$

by the following equation:

$$\vec{v} = \frac{t_1|\vec{y}|^2 - t_2\vec{x}\cdot\vec{y}}{t_2^2|\vec{x}|^2 + t_1^2|\vec{y}|^2 - t_1t_2\vec{x}\cdot\vec{y}}\vec{x} + \frac{t_2|\vec{x}|^2 - t_1\vec{x}\cdot\vec{y}}{t_2^2|\vec{x}|^2 + t_1^2|\vec{y}|^2 - t_1t_2\vec{x}\cdot\vec{y}}\vec{y}$$

where $\vec{x}=\vec{AB}$, $\vec{y}=\vec{AC}$, $t_1=Bt-At$, $t_2=Ct-At$, and At, Bt, Ct are excitation wave passing times at said three adjacent electrodes.

4. An intracardiac potential analyzing apparatus according to claim 3, wherein said means for calculating a vector includes means for measuring said excitation wave passing times At, Bt, Ct corresponding to an order in which excitation has actually passed said three selected electrodes.

5. An intracardiac potential analyzing apparatus according to claim 3, wherein, assuming that an arrythmia has a period CL, and that said excitation wave passing times At, Bt, Ct are earlier in the order of At, Bt, Ct, said means for measuring said excitation wave passing times At, Bt, Ct includes means for adding CL to At to derive a new At and substituting the new At into said vector calculation equation when $Bt-At \geq CL/2$ and $Ct-Bt<CL/2$ are satisfied, and for adding CL to At and Bt, respectively, to derive a new At and a new Bt and substituting the new At and the new Bt into said vector calculation equation when $Bt-At<CL/2$ and $Ct-Bt \geq CL/2$ are satisfied.

6. An intracardiac potential analyzing apparatus according to claim 2, wherein said means for selecting a plurality of sets of electrodes includes means for selecting said plurality of sets of electrodes from a plurality of electrodes corresponding to excitation points within a predetermine time width.

7. An intracardiac potential analyzing apparatus according to claim 6, wherein said means for selecting a plurality of sets of electrodes includes means for selecting sets of said electrodes while sequentially shifting said predetermined time width by an shift amount, said shift amount being a shorter time period than said predetermined time width, and said means for displaying includes means for sequentially displaying said plurality of calculated vectors for every said predetermined time width in an animation manner.

8. An intracardiac potential analyzing apparatus according to claim 1, wherein said means for displaying includes means for selecting and displaying vectors associated with said calculated excitation waves having a speed within a predetermined range.

9. An intracardiac potential analyzing method utilizing a computer, comprising the steps of:

registering a relative positional relationship among a plurality of electrodes in a memory as a coordinate map;

selecting a plurality of sets of three adjacent electrodes from among said plurality of electrodes;

calculating a vector of an excitation wave which has passed said three adjacent electrodes for each of said plurality of sets of three adjacent electrodes; and displaying said plurality of calculated vectors in association with said coordinate map.

10. An intracardiac potential analyzing method according to claim 9, wherein said step of calculating a vector includes a step of calculating the vector of said excitation wave from positional information on said three selected adjacent electrodes, and excitation waves passing times from a reference time, serving as a reference, to times at which an excitation wave passes said three selected electrodes, said reference time being arbitrarily set on a time axis of an electrocardiogram.

11. An intracardiac potential analyzing method according to claim 10, wherein said step of calculating a vector includes a step of setting positions of three electrodes in an orthogonal three-dimensional coordinate system defined by three mutually orthogonal x-, y-, and z-axes as A(Ax, Ay, Az), B(Bx, By, Bz), and C(Cx, Cy, Cz), and calculating an excitation wave vector:

$$\vec{v} = v(v_x, v_y, v_z)$$

by the following equation:

$$\vec{v} = \frac{t_1|\vec{y}|^2 - t_2\vec{x}\cdot\vec{y}}{t_2^2|\vec{x}|^2 + t_1^2|\vec{y}|^2 - t_1t_2\vec{x}\cdot\vec{y}}\vec{x} + \frac{t_2|\vec{x}|^2 - t_1\vec{x}\cdot\vec{y}}{t_2^2|\vec{x}|^2 + t_1^2|\vec{y}|^2 - t_1t_2\vec{x}\cdot\vec{y}}\vec{y}$$

where $\vec{x}=\vec{AB}$, $\vec{y}=\vec{AC}$, $t_1=Bt-At$, $t_2=Ct-At$, and At, Bt, Ct are excitation wave passing times at said three adjacent electrodes.

12. An intracardiac potential analyzing method according to claim 11, wherein said step of calculating a vector includes a step of measuring said excitation wave passing times At, Bt, Ct corresponding to an order in which excitation has actually passed said three selected electrodes.

13. An intracardiac potential analyzing method according to claim 12, wherein, assuming that an arrythmia has a period CL, and that said excitation wave passing times At, Bt, Ct are earlier in the order of At, Bt, Ct, said step of measuring said excitation wave passing times At, Bt, Ct includes a step of adding CL to At to derive a new At and substituting the new At into said vector calculation equation when Bt−At≧CL/2 and Ct−Bt<CL/2 are satisfied, and of adding CL to At and Bt, respectively, to derive a new At and a new Bt and substituting the new At and the new Bt into said vector calculation equation when Bt−At<CL/2 and Ct−Bt≧CL/2 are satisfied.

14. An intracardiac potential analyzing method according to claim 9, wherein said step of selecting a plurality of sets of electrodes includes a step of selecting said plurality of sets of electrodes from a plurality of electrodes corresponding to excitation points within a predetermine time width.

15. An intracardiac potential analyzing method according to claim 14, wherein said step of selecting a plurality of sets of electrodes includes a step of selecting sets of said electrodes while sequentially shifting said predetermined time width by an shift amount, said shift amount being a shorter time period than said predetermined time width, and said step of displaying includes a step of sequentially displaying said plurality of calculated vectors for every said predetermined time width in an animation manner.

16. An intracardiac potential analyzing method according to claim 9, wherein said step of displaying includes a step of selecting and displaying vectors associated with said calculated excitation waves having a speed within a predetermined range.

17. A computer readable medium having recorded thereon a program for causing a computer to execute an intracardiac potential analyzing method, comprising the steps of:
  registering a relative positional relationship among a plurality of electrodes as a coordinate map;
  selecting a plurality of sets of three adjacent electrodes from among said plurality of electrodes;
  calculating a vector of an excitation wave which has passed said three adjacent electrodes for each of said plurality of sets of three adjacent electrodes; and
  displaying said plurality of calculated vectors in association with said coordinate map.

18. A computer readable medium according to claim 17, wherein said step of calculating a vector includes a step of calculating the vector of said excitation wave from positional information on said three selected adjacent electrodes, and excitation waves passing times from a reference time, serving as a reference, to times at which an excitation wave passes said three selected electrodes, said reference time being arbitrarily set on a time axis of an electrocardiogram.

19. A computer readable medium according to claim 18, wherein said step of calculating a vector includes a step of setting positions of three electrodes in an orthogonal three-dimensional coordinate system defined by three mutually orthogonal x-, y-, and z-axes as A(Ax, Ay, Az), B(Bx, By, Bz), and C(Cx, Cy, Cz), and calculating an excitation wave vector:

$$\vec{v}=v(v_x,v_y,v_z)$$

by the following equation:

$$\vec{v} = \frac{t_1|\vec{y}|^2 - t_2\vec{x}\cdot\vec{y}}{t_2^2|\vec{x}|^2 + t_1^2|\vec{y}|^2 - t_1t_2\vec{x}\cdot\vec{y}}\vec{x} + \frac{t_2|\vec{x}|^2 - t_1\vec{x}\cdot\vec{y}}{t_2^2|\vec{x}|^2 + t_1^2|\vec{y}|^2 - t_1t_2\vec{x}\cdot\vec{y}}\vec{y}$$

where $\vec{x}=\vec{AB}$, $\vec{y}=\vec{AC}$, $t_1=Bt-At$, $t_2=Ct-At$, and At, Bt, Ct are excitation wave passing times at said three adjacent electrodes.

20. A computer readable medium according to claim 19, wherein said step of calculating a vector includes a step of measuring said excitation wave passing times At, Bt, Ct corresponding to an order in which excitation has actually passed said three selected electrodes.

21. A computer readable medium according to claim 20, wherein, assuming that an arrythmia has a period CL, and that said excitation wave passing times At, Bt, Ct are earlier in the order of At, Bt, Ct, said step of finding said excitation wave passing times At, Bt, Ct includes a step of adding CL to At to derive a new At and substituting the new At into said vector calculation equation when Bt−At≧CL/2 and Ct−Bt<CL/2 are satisfied, and of adding CL to At and Bt, respectively, to derive a new At and a new Bt and substituting the new At and the new Bt into said vector calculation equation when Bt−At<CL/2 and Ct−Bt≧CL/2 are satisfied.

22. A computer readable medium according to claim 17, wherein said step of selecting a plurality of sets of electrodes includes a step of selecting said plurality of sets of electrodes from a plurality of electrodes corresponding to excitation points within a predetermine time width.

23. A computer readable medium according to claim 22, wherein said step of selecting a plurality of sets of electrodes includes a step of selecting sets of said electrodes while sequentially shifting said predetermined time width by an shift amount, said shift amount being a shorter time period than said predetermined time width, and said step of displaying includes a step of sequentially displaying said plurality of calculated vectors for every said predetermined time width in an animation manner.

24. A computer readable medium according to claim 17, wherein said step of displaying includes a step of selecting and displaying vectors associated with said calculated excitation waves having a speed within a predetermined range.

25. A computer readable data recording medium comprising:
  a first region having stored thereon a program for reading recorded data;
  a second region having stored thereon relative positional relationship among a plurality of electrodes;
  a third region having stored thereon vector data on excitation waves calculated in association with a plurality of sets of three adjacent electrodes within said electrodes; and
  a fourth region having stored thereon a program for displaying on a display device a plurality of vectors based on said vector data in association with positions of said sets of three electrodes used to calculate said vectors.

* * * * *

UNITED STATES PATENT AND TRADEMARK OFFICE
CERTIFICATE OF CORRECTION

PATENT NO.    : 6,360,121 B1
DATED         : March 19, 2002
INVENTOR(S)   : Morio Shoda et al.

It is certified that error appears in the above-identified patent and that said Letters Patent is hereby corrected as shown below:

Column 10,
Line 18, replace "predetermine" with -- predetermined --

Column 12,
Line 55, insert -- as a coordinate map -- after "electrodes"
Line 56, insert -- an -- after "on"
Line 57, replace "waves" with -- wave --
Line 62, replace "positions" with -- the coordinate map --

Signed and Sealed this

Nineteenth Day of November, 2002

Attest:

JAMES E. ROGAN
Attesting Officer    Director of the United States Patent and Trademark Office